(12) United States Patent
Sanchez Pina et al.

(10) Patent No.: US 6,907,353 B2
(45) Date of Patent: Jun. 14, 2005

(54) APPARATUS AND METHOD FOR MEASURING FLUID CHARACTERISTICS

(75) Inventors: Jose L. Sanchez Pina, Chihuahua (MX); Ramon A Sanchez, Chihuahua (MX)

(73) Assignee: Delphi Technologies, Inc., Troy, MI (US)

( * ) Notice: Subject to any disclaimer, the term of this patent is extended or adjusted under 35 U.S.C. 154(b) by 76 days.

(21) Appl. No.: 10/602,383

(22) Filed: Jun. 24, 2003

(65) Prior Publication Data

US 2004/0267465 A1 Dec. 30, 2004

(51) Int. Cl.⁷ .................................................. G01F 1/00
(52) U.S. Cl. ............................. 702/30; 702/45; 702/47; 702/50; 73/304 C
(58) Field of Search .............................. 702/30, 50, 45, 702/47, 24, 25, 27, 31, 32, 52, 55, 114, 130, 138, 140, 136, 183, 100; 73/1.16, 1.25, 1.26, 1.34, 1.35, 1.57, 1.59, 35.02, 35.04, 37, 53.01, 53.04, 53.05, 54.01, 54.02, 290 R, 54.05, 54.07, 54.09, 54.11, 54.13, 54.14, 61.73, 152.18, 152.21, 152.22, 152.29, 861.02, 861.03, 861.08, 861.12, 861.14, 861.15, 861.354, 861.356, 861.357, 304 C, 195, 118.2; 340/612, 618, 603, 606, 611; 700/266, 281, 282; 701/99, 102, 104; 324/663, 664, 667, 665, 698

(56) References Cited

U.S. PATENT DOCUMENTS

| 5,604,441 | A | * | 2/1997 | Freese et al. ................ 324/663 |
| 6,138,508 | A | * | 10/2000 | Hannan et al. ............ 73/304 C |
| 6,381,548 | B1 | | 4/2002 | Van Marion et al. .......... 702/45 |
| 6,498,566 | B1 | | 12/2002 | Lin ............................ 340/612 |
| 6,508,233 | B1 | * | 1/2003 | Suhre et al. ................. 123/478 |
| 6,539,797 | B2 | * | 4/2003 | Livingston et al. ........ 73/304 C |
| 6,578,416 | B1 | * | 6/2003 | Vogel et al. ............... 73/304 C |
| 2004/0060344 | A1 | * | 4/2004 | Kauffman et al. .......... 73/53.01 |
| 2004/0107055 | A1 | * | 6/2004 | Kolosov et al. .............. 702/25 |

* cited by examiner

*Primary Examiner*—Hal Wachsman
(74) *Attorney, Agent, or Firm*—Jimmy L. Funke

(57) ABSTRACT

A sensing element for use with a controller adapted to receive input signals corresponding to the sensing element, the sensing element having: a housing defining a conduit adapted to be in fluid communication with a fluid; a pair of sensing arrays disposed within the conduit, the pair of sensing arrays being in a facing spaced relationship to define a gap disposed therebetween; a plurality of sensors disposed on the pair of sensing arrays, the plurality of sensors being adapted to sense and provide signals corresponding to a plurality of parameters of the fluid; a microprocessor adapted to receive the signals of the plurality of sensors, the microprocessor being adapted to determine at least one condition of the fluid upon receipt of the signals corresponding to the plurality of parameters of the fluid.

9 Claims, 2 Drawing Sheets

APPARATUS AND METHOD FOR MEASURING FLUID CHARACTERISTICS

TECHNICAL FIELD

The present disclosure generally relates to an apparatus and system for measuring fluid characteristics.

BACKGROUND

The measurement of viscosity in automotive, medical, agricultural and industrial applications is important to determine some fluid characteristics that may be related to the fluids performance as a fuel, lubricate, cooling, biological solvent and/or a carrier of substances in different applications.

Currently, several technologies are used to measure viscosity for example, vibrating and frequency excited devices use the principal of a dampening effect to determine the resistance of a fluid to shear stresses, which is then correlated to viscosity. This method is widely used. However, it requires a controller for excitation and is very dependent upon temperature variations and fluid composition.

Another example of technologies used to measure viscosity is microwave propagation in fluid medium. This method is accurate and reliable however, this method also requires a controller and considerable investment in order to accommodate it in smaller packages. In addition, it is also very dependent upon fluid composition. Yet another example of technologies used to measure viscosity is optical detection devices. These are also accurate in a controlled fluid medium. However, it is very dependent upon the fluid composition and its reliability as a sensor is hindered by the formation of solid particles that may obstruct the clearance of the optical sensing element. In addition, this technology is very expensive and is typically used in medical and/or industrial applications.

A common point or disadvantage associated with the aforementioned sensing technologies is that they operate better under low dynamic flow rates or in a completely static state of the medium.

SUMMARY

The present disclosure is related to a system that combines reliable and inexpensive technologies to measure different fluid parameters such as viscosity, temperature, density and changes in the dielectric properties of the fluid in order to determine its condition in a dynamic flow environment.

The present disclosure also uses the measurement of mechanical properties of the sensing element in this dynamic environment in order to determine the flow rate of the fluid.

A sensing element for use with a controller adapted to receive input signals corresponding to the sensing element, the sensing element comprising: a housing defining a conduit adapted to be in fluid communication with a fluid; a pair of sensing arrays disposed within the conduit, the pair of sensing arrays being in a facing spaced relationship to define a gap disposed therebetween; a plurality of sensors disposed on the pair of sensing arrays, the plurality of sensors being adapted to sense and provide signals corresponding to a plurality of parameters of the fluid; a microprocessor adapted to receive the signals of the plurality of sensors, the microprocessor being adapted to determine at least one condition of the fluid upon receipt of the signals corresponding to the plurality of parameters of the fluid.

DETAILED DESCRIPTION

Figure 1:
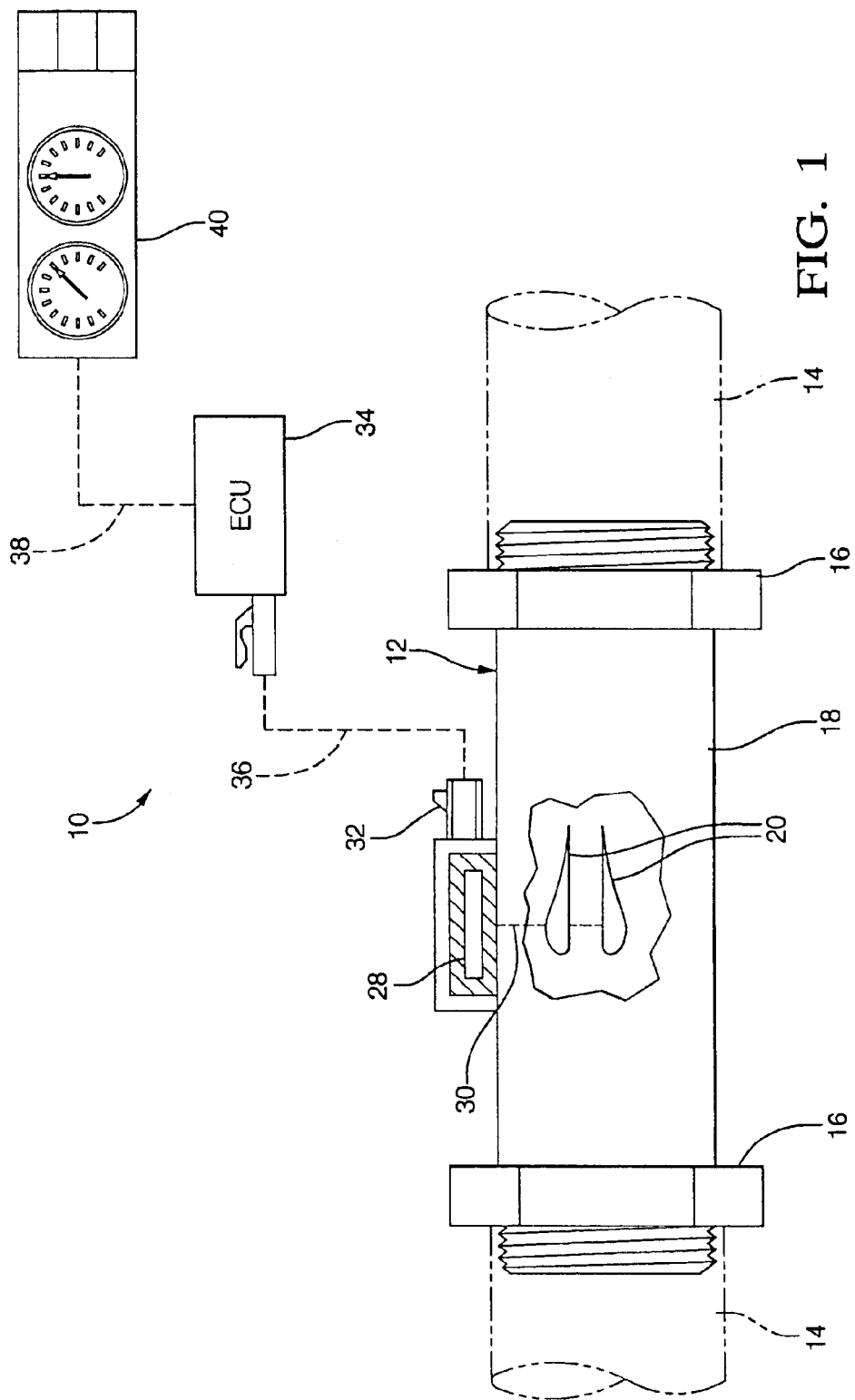
FIG. 1 is a schematic illustration of a fluid sensing system of an exemplary embodiment of the present disclosure.

Referring now to FIG. 1, an intended use of the fluid condition and flow determination system of the present disclosure is illustrated schematically. In accordance with an exemplary embodiment the fluid condition and flow determination system is adapted for use with a fluid that is in a dynamic state (e.g., flowing). The system is configured to determine the flow and condition of the fluid as it passes by the sensing element of the present disclosure. Of course, the system can also be used to provide fluid conditions in static states. In accordance with an exemplary embodiment the fluid condition and flow determination system is contemplated for use in a vehicular application. Of course, it is also contemplated that the fluid condition and flow determination system of the present disclosure is capable of being used in numerous applications for example, industrial, oil refineries, agricultural, manufacturing, processing and any other application wherein the fluid condition and flow determination of a fluid is desired.

As discussed herein fluid condition relates to specific fluid parameters including but not limited to the following: capacitance, conductivity, the presence or lack thereof of metals, biological materials and other materials and/or contaminants.

As illustrated in FIG. 1, a sensing array or sensing assembly 12 of the system is attached to and positioned within a fluid line 14 by means of a pair of connectors 16 disposed at either end of the assembly. The sensing assembly comprises a housing 18 that acts as a conduit to transfer mass between both ends of the sensing assembly. A pair of shaped electrodes or arrays 20 are positioned within the conduit defined by housing 18. In an exemplary embodiment, the shaped electrodes comprise a wing shape (FIG. 2) and are fixedly secured within the conduit defined by housing 18. Thus, there is no movement of the shaped electrodes within the housing.

The shaped electrodes or wings 20 are positioned in a parallel relationship with respect to each other in order to provide a gap disposed therebetween to measure changes in the dielectric constant and/or the conductivity of a fluid that passes through the gap. In accordance with an exemplary embodiment the shaped electrodes or wings are constructed out of a material that is non-corrosive and will not affect the performance of the sensor positioned therein. An example of such a material is 301 stainless steel. Of course, other materials are contemplated to be used with the sensing system of the present disclosure, such materials include but are not limited to the following; plastics, metals and alloys. In addition, the dimension of the wings in one direction may be around 6–7 mm allowing for the assembly to be placed within small fluid lines. Of course, and as applications vary, these dimensions may be greater or less than 6–7 mm.

The hydrodynamic or aerodynamic configurations of the wings or shaped electrodes are predetermined and are known constants for use in formulas stored in the memory of a microprocessor adapted for use with the system. In addition, the distance between the two wings is also predetermined and is a known constant for use in formulas stored in the memory of a microprocessor adapted for use with the system.

Figure 2:
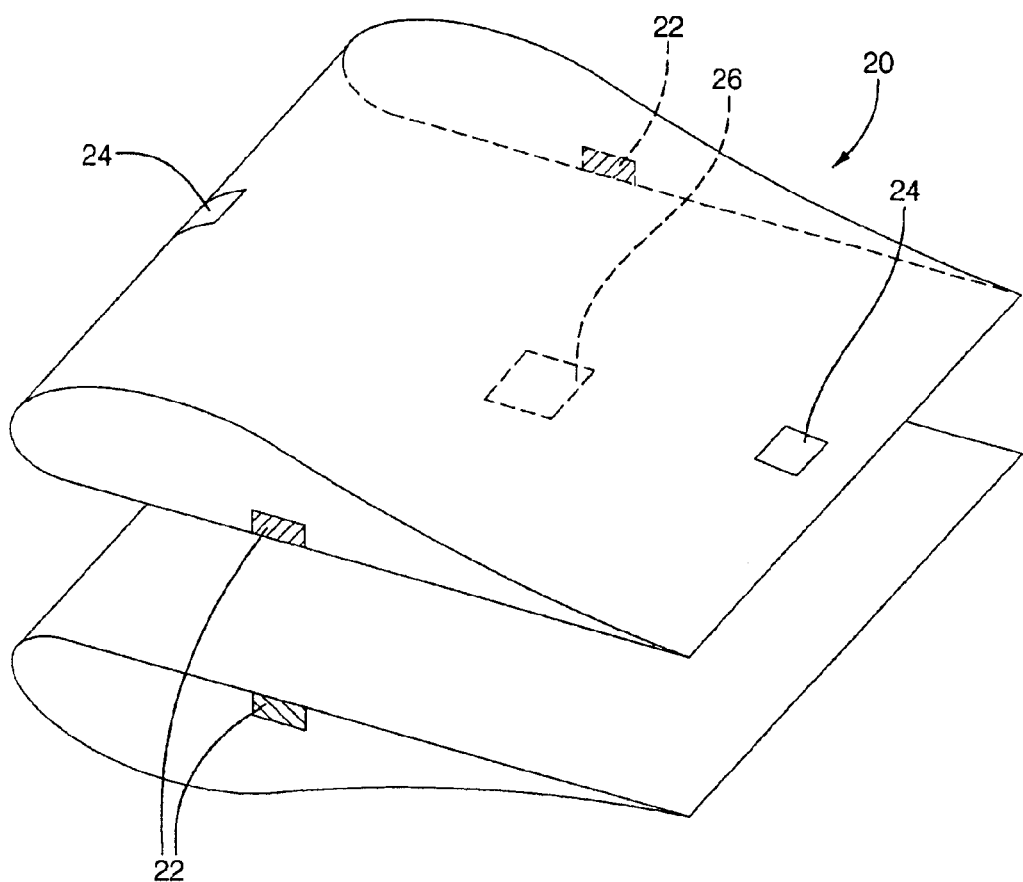
FIG. 2 is a perspective view of a portion of a sensing element of the present disclosure.

Referring now to FIG. 2, force sensors 22 are connected to each of the electrodes in order to determine the stress at the base of these sensing parts. The value of the stresses can be correlated to the drag force of the shaped electrodes which in turn can determine the velocity of the fluid moving past them. The speed of the fluid and the information about the sectional area of the sensing housing (e.g., area) determine the flow rate of the fluid by using standard equations stored in the memory of a microprocessor adapted for use with the system.

This information is useful in the dynamic conditions or applications of the fluid that the fluid system is in fluid communication with. For example, in the case of fuel being supplied to an engine or other machine passing through the system, the sensing system can determine the consumption rate by determining the flow rate through the sensing assembly. Of course, it is noted that the aforementioned is but an example of an intended use and the present disclosure is not intended to be limited to such an arrangement.

In addition to the force sensors, pressure sensors 24 are also located on the external upper surfaces of the wing electrodes and an internal surface pressure and temperature sensor 26 is disposed within at least one if not both of the electrodes. The pressure and temperature sensors in the internal area of the array determine the pressure differential, which enables a system to determine the viscosity of the fluid.

In order to determine the fluid condition, a pair of electrodes or wings 20 are disposed in a facing space relationship wherein fluid conditions can be determined by the sensors disposed on one or both of the wings 20. For example, capacitance is determined by the parallel electrodes, as if they were two plates, using the formula C=E(K A/d) wherein C=capacitance in picofarads (pF), E=a constant known as the absolute permitivity of free space, K=relative dielectric constant of the insulating material, A=effective area of the conductors and d=distance between conductors.

Accordingly, and if the sensing assembly is disposed in a fuel and ethanol or some other substance is added to the fuel the added substance changes the dielectric constant of the insulating material (K). For example, the dielectric constant of a petroleum derived fuel is around 1.8 to 2.5, the dielectric constant of the alcohol is around 19, so even small quantities of ethanol in gasoline can be detected. In order to detect traces of metals or minerals, the controller or control algorithm of the RAM or look up tables used with the sensing assembly will be calibrated to detect small changes in dielectric constant of the fluid being measured (e.g., fuels and the changes associated with different contaminants). Therefore, the changes of certain fluids associated with certain contaminants have to be characterized in order to obtain their behavior to be able to detect them.

Thus, fluid capacitance is determined by measuring the dielectric constant of the fluid passing between the two electrodes. Also, the presence or lack thereof of metals (e.g., contaminants or desired materials) in the fluid is determined by measuring the conductivity of the same. The conductivity can be determined by using high frequency signals to induce a voltage in one electrode and measure the voltage in the other electrode wherein the voltages are measured by sensors on the electrodes. Also, the presence or lack thereof of biological or non-metals (e.g., contaminants or desired materials) in the fluid can be determined by measuring the characteristics of the same, for example, by measuring fluid capacitance, which is affected by the presence or lack thereof of certain contaminants or desired materials. These measurements are then compared to known values of known fluid to determine the presence and percentage of the materials.

The sensing assembly when determining the capacitance and/or conductivity as well as the viscosity of the fluids passing through the housing uses the sensor's temperature readings in order to compensate its determined values due to thermal variations of the fluid. These temperature readings will be inputted into the desired formulas wherein temperature affects the resulting value (e.g., viscosity).

In addition, the two wings or electrodes provide the system with a means for double checking the determined flow rate by disposing a differential pressure sensor on both electrodes wherein one sensor and one electrode is capable of determining the flow rate thus, the other is capable of providing a reference valve for comparison.

Referring again to FIG. 2, each of the aforementioned sensors are connected to an electronic circuit board 28 via a signal line 30 or a plurality of signal lines 30 adapted to transmit signals of the sensors to the circuit board. Of course, other means of communication of this information are contemplated to be within the scope of the present disclosure (e.g., optical, radio frequency and other equivalent means of signal transfer).

The electronics circuit board is sealed from the environment by a PCB seal (glass or epoxy), which will protect the same from contaminants in the environment which assembly 12 displaced. In one embodiment the entire assembly is placed within the fluid wherein signals are transmitted to the control module via radio frequency or other means for providing the appropriate signals to the controller. Thus, if the entire assembly is placed within a fluid transfer medium the seal will protect the circuit board from the fluid.

Alternatively, if the conduit is attached to or comprises a portion of a fluid communication means, the electronics circuit board is disposed on the exterior of the conduit, and the electric circuit board is still sealed from the environment by a PCB seal (glass or epoxy), which will protect the electronics circuit board from contaminants.

The electronics circuit board is connected by means of a harness 32 to an engine control module 34 via a signal line 36 which processes the information and sends a signal, via a signal line 38 to a display 40, on a dashboard of the vehicle (not shown) or other location if the device is used in a non-vehicular application. The signals on the display may be related to fluid condition (such as different fuel blends or engine oil) and fluid flow rate (which could be translated to fuel consumption), which are then presented in a readable format for an operator of the vehicle.

In accordance with an exemplary embodiment the engine control module 34 and electronic circuit board 28 is/are an onboard chip such as a digital signal processor, capable of executing logic stored on the processor in the form of a readable computer code. The logic includes a series of computer-executable instructions, which will allow the engine control module 34 and electronic circuit board 28 to determine the fluid flow and fluid condition (e.g., viscosity, capacitance, conductivity etc.) of the fluid passing by the electrodes.

These formula and instructions may reside, for example, in RAM or look up tables of the engine control module 34 and electronic circuit board 28. Alternatively, the instructions may be contained on any equivalent data storage device with a computer readable medium, such as a computer diskette, magnetic media, conventional hard disk drive, electronic read-only memory, optical storage device, or other appropriate data storage device. The instructions and formula will also include sufficient data to determine the presence of certain materials in the fluid by measuring the dielectric constant and comparing the results to known values of the fluid thus, the presence of certain materials or lack thereof is capable of being determined by the sensing assembly of the present disclosure.

In accordance with an exemplary embodiment of the present disclosure, the electrodes are positioned within housing 18 and the plurality of sensors are positioned to obtain readings (e.g., force or tension, pressure, temperature, etc.), which are related to the fluid passing by the two electrodes or wings. The readings are then inputted into a plurality of formulas stored in the memory of the electronic circuit board 28 or alternatively the engine control module 34. The formulas are known mathematical equations that are also provided with constants, which correspond to the particular configurations of the sensing system and are necessary for providing the desired output from the formula when the required parameters are sensed. For example, the cross sectional area of housing 18 is known and stored in the data or formulas, the configuration and dimension of the wings is known and stored in the data or formulas, the type of the sensors on the wings is known and stored in the data or formulas, the distance or gap between the wings is known and stored in the data or formulas.

Accordingly, and once provided with the data from the sensors disposed on the wings, the system will be able to determine the fluid condition and fluid flow as it passes by the sensing array. In addition, and as an alternative embodiment and wherein the system is disposed within a vehicle, the executable code is adapted to only take readings when the vehicle engine is running.

In one embodiment the exterior surface of the electrodes or wings 20 is smooth in order to provide a flow about the two electrodes for creating a desirable environment in which the parameters are to be measured. In an alternative embodiment, the exterior surface of the electrodes or wings 20 is configured to be rough or un-smooth.

An example of a particular use is in a vehicular application wherein the sensing assembly is adapted to determine the characteristics of the fuel being supplied to the engine wherein the sensing assembly can determine the presence of fuel additives by measuring particular parameters, which are indicative of varying fuel blends (e.g., the presence of ethanol, or other fuel additives) wherein the detection of such an additive is provided as a signal to the engine control module wherein the engine control module adapts the engines performance (e.g., varying the spark duration or timing of the spark firing) in order to more efficiently burn the fuel. Of course, the aforementioned is but an example of an intended use and the present disclosure is not intended to be limited by the same.

Advantages of the sensing system of the present disclosure is that it operates under dynamic conditions of the fluid (e.g., flowing past the sensing array) and it provides valuable information pertaining to the fluid as it is being transported to the location in which it is going to be used. In order to accommodate this, the sensing assembly is disposed with the conduit providing the fluid path of the fluid.

Thus, the sensing assembly is designed and constructed to have a small package that allows its installation directly on, within or part of the fluid transportation lines. The package of the sensor is designed to increase its manufacturability and eases the process of installation in fuel, oil or cooling fluid transportation lines.

For example, and when the sensing assembly is used in a fuel system of an engine of a vehicle, the sensing assembly is able to provide fluid parameters to the engine control module, which may adapt the engines performance based upon the sensed parameters. In this embodiment the sensing assembly is positioned between fuel tank and fuel pump thus, the dynamic conditions of the fuel are capable of being sensed.

In addition, and since the sensing assembly is measuring the fluid in a dynamic state, the actual condition of the fluid (e.g., mixed, stirred, turbulent) being received by the engine is being sampled by the assembly. Thus, an accurate reading of the fluid characteristics is being provided. Moreover, assembly can be adapted to provide continuous reading thus, as the flow rate or dynamic conditions change the assembly provides readings commensurate with such a state.

Additionally, the sensing assembly is also adapted to measure the condition of the fluid that may be correlated to contamination and/or change in its chemical composition. Also, and since the shaped electrodes are in a fixed position, the sensing assembly has no moving parts in order to measure the fluid's viscosity.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the present disclosure not be limited to the particular embodiment disclosed as the best mode contemplated for carrying out this invention, but that the invention will include all embodiments falling within the scope of the appended claims.

What is claimed is:

1. A sensing element for use with a controller adapted to receive input signals corresponding to the sensing element, said sensing element comprising:

a housing defining a conduit adapted to be in fluid communication with a fluid;

a pair of sensing arrays disposed within said conduit, said pair of sensing arrays being in a facing spaced relationship to define a gap disposed therebetween;

a plurality of sensors disposed on said pair of sensing arrays, said plurality of sensors being adapted to sense and provide signals corresponding to a plurality of parameters of said fluid, wherein the plurality of parameters include temperature, pressure differential exerted on a sensing array of the pair of sensing arrays, and force exerted on the sensing array; and a microprocessor adapted to receive the signals of said plurality of sensors, said microprocessor being adapted to determine at least one condition of said fluid upon receipt of the signals corresponding to the plurality of parameters of said fluid.

2. The sensing element as in claim 1, wherein the pair of sensing arrays are wing shaped.

3. The sensing element as in claim 2, wherein at least one of the sensors of said plurality of sensors is disposed on the leading edge of one of the sensing arrays.

4. The sensing element as in claim 2, wherein the pair of sensing arrays are stainless steel.

5. The sensing element as in claim 1, wherein a pressure differential signal is used by the microprocessor to determine the flow rate of said fluid flowing through said housing.

6. The sensing element as in claim 5, wherein the pressure differential signal of one sensing array of said pair of sensing arrays is used by the microprocessor to determine the flow rate of said fluid flowing through said housing and the pressure differential signal of the other sensing array of said pair of sensing arrays is used by the microprocessor to check the flow rate determined by the microprocessor.

7. The sensing element as in claim 1, wherein one of the plurality of sensors is disposed within one of the pair of sensing arrays.

8. A sensing element for use with a controller adapted to receive input signals corresponding to the sensing element, said sensing element comprising:

a housing defining a conduit adapted to be in fluid communication with a fluid;

a pair of sensing arrays disposed within said conduit, said pair of sensing arrays being in a facing spaced relationship to define a gap disposed therebetween;

a plurality of sensors disposed on said pair of sensing arrays, said plurality of sensors being adapted to sense and provide signals corresponding to a plurality of parameters of said fluid; and a microprocessor adapted to receive the signals of said plurality of sensors, said microprocessor being adapted to determine at least one condition of said fluid upon receipt of the signals corresponding to the plurality of parameters of said fluid;

wherein the pair of sensing arrays and the plurality of sensors are adapted to provide signals to the microprocessor wherein the microprocessor is adapted to determine the conductivity of the fluid flowing between the pair of sensing arrays.

9. The sensing element as in claim 8, wherein one of the plurality of sensors is disposed within one of the pair of sensing arrays.

* * * * *